(12) United States Patent
Wu et al.

(10) Patent No.: US 8,193,226 B2
(45) Date of Patent: Jun. 5, 2012

(54) CANDESARTAN CILEXETIL

(75) Inventors: Qiaomei Wu, Zhejiang (CN); Huiyan Gao, Zhejiang (CN); Hao Chen, Zhejian (CN); Qiping Yan, Zhejiang (CN); Junqing Peng, Zhejiang (CH); Gongyun Hu, Zhejiang (CH)

(73) Assignees: Zhejiang Huahai Pharmaceutical Co., Ltd. (CN); Alfred E. Tiefenbacher GmbH & Co. KG (DE)

( * ) Notice: Subject to any disclaimer, the term of this patent is extended or adjusted under 35 U.S.C. 154(b) by 222 days.

(21) Appl. No.: 12/740,831

(22) PCT Filed: Oct. 27, 2008

(86) PCT No.: PCT/EP2008/009065
§ 371 (c)(1),
(2), (4) Date: Apr. 30, 2010

(87) PCT Pub. No.: WO2009/056266
PCT Pub. Date: May 7, 2009

(65) Prior Publication Data
US 2010/0267785 A1   Oct. 21, 2010

(30) Foreign Application Priority Data

Oct. 30, 2007   (DE) .......................... 10 2007 052 070

(51) Int. Cl.
*A61K 31/41* (2006.01)
*A61K 9/20* (2006.01)
*A61K 9/26* (2006.01)

(52) U.S. Cl. .......................... 514/381; 424/465; 424/470

(58) Field of Classification Search .................. 514/381; 424/465, 470
See application file for complete search history.

(56) References Cited

U.S. PATENT DOCUMENTS

| | | | |
|---|---|---|---|
| 3,145,146 | A | 8/1964 | Leibernam et al. |
| 2001/0009678 | A1 | 7/2001 | Toshihiro et al. |
| 2007/0014854 | A1 | 1/2007 | Zalit et al. |

FOREIGN PATENT DOCUMENTS

| | | |
|---|---|---|
| EP | 0546358 A2 | 6/1993 |
| EP | 1203580 A1 | 5/2002 |
| EP | 1329217 A1 | 7/2003 |
| EP | 1952806 A1 | 8/2008 |
| WO | 9738960 A1 | 10/1997 |
| WO | 0006126 A1 | 2/2000 |
| WO | 0162230 A1 | 8/2001 |
| WO | 2005070398 A2 | 8/2005 |
| WO | 2005079751 A2 | 9/2005 |
| WO | 2005084648 A1 | 9/2005 |
| WO | 2008030161 A1 | 3/2008 |
| WO | 2008077823 A1 | 7/2008 |

OTHER PUBLICATIONS

Office Action from German Application No. 102007052070.2 dated Nov. 14, 2008.
International Search Report PCT/EP2008/009065, dated Jun. 4, 2009.

*Primary Examiner* — Raymond Henley, III
(74) *Attorney, Agent, or Firm* — Lerner, David, Littenberg, Krumholz & Mentlik, LLP

(57) ABSTRACT

Candesartan cilexetil-containing granules which include a sugar alcohol and a binder and which are produced by granulation with an alcoholic granulating liquid. The granules are suitable for producing tablets in which the candesartan cilexetil is present in a form stabilized with regard to decomposition.

12 Claims, No Drawings

CANDESARTAN CILEXETIL

CROSS REFERENCE TO RELATED APPLICATIONS

The present application is a national phase entry under 35 U.S.C. §371 of International Application No. PCT/EP2008/009065 filed Oct. 27, 2008, published in German, which claims the benefit of German Patent Application No. 10 2007 052 070.2, filed Oct. 30, 2007. The disclosures of said applications are incorporated by reference herein.

The present invention relates to solid, orally administered pharmaceutical compositions, which contain candesartan cilexetil as active ingredient in a form stabilized against decomposition. Furthermore, the invention relates to a method for preparing such stable pharmaceutical compositions.

Candesartan is an angiotensin II receptor antagonist used mainly for the treatment of hypertension. It is marketed in the form of its prodrug candesartan cilexetil as a tablet under the brand names Blopress or Atacand. Despite its administration as a prodrug, candesartan cilexetil only has low bioavailability of 15% (tablet) or 40% (solution). We also know that the drug candesartan cilexetil, as such, i.e. in isolated form, is indeed stable when exposed to increased temperatures, humidity and light, but when processed into a tablet, that is, in the presence of other pharmaceutically acceptable additives, or in the production of a pharmaceutical composition, for example at granulation or tableting, it tends to decompose.

EP 0 546 358 proposes the incorporation of an oily substance with a low melting point to stabilize pharmaceutical compositions containing candesartan cilexetil as a solution to the above-mentioned stability problem. The oily substances should have a melting point of about 20 to 90° C. They can be either soluble or insoluble in water. Examples mentioned of such oily substances are specifically hydrocarbons, higher fatty acids, higher alcohols, fatty esters of polyhydric alcohols, higher alcohol ethers of polyhydric alcohols and polymers or copolymers of alkylene oxides. The oily substance with a low melting point can for example in powder form be mixed with candesartan cilexetil and then granulated and dried. Alternatively, the oily substance can be dissolved in a suitable solvent and the resulting solution can then be mixed with candesartan cilexetil, kneaded, granulated and dried. As a preferred embodiment, polyethylene glycol 6000 as oily substance is mixed with candesartan cilexetil, and then the mixture is granulated with an aqueous granulating liquid containing hydroxypropyl cellulose as binder.

As an alternative to the use of an oily substance, WO 2005/079751 discloses lipids and phospholipids as stabilizers for pharmaceutical compositions containing candesartan cilexetil. According to WO 2005/079751, lipids include fatty acids and fatty acid esters. The lipids, phospholipids and mixtures thereof are intended to be used in a concentration of about 0.5 to about 10 wt %, based on the total weight of the pharmaceutical composition.

WO 2005/070398 also discloses fatty acid esters for stabilizing pharmaceutical compositions containing candesartan cilexetil. Because of the insolubility of candesartan cilexetil in water, using a co-solvent is proposed that should be present in an amount of 1 to 10 wt % in the pharmaceutical composition. The addition of a co-solvent should increase the bioavailability of the active ingredient by increasing the solubility and dissolution rate of the active ingredient in aqueous solutions. In particular propylene glycol, polyethylene glycol, ethanol, glycerol, propylene glycol esters, polyethylene glycol ester and mixtures thereof are proposed as co-solvents.

WO 2005/084648 discloses, however, that pharmaceutical compositions containing candesartan cilexetil can be stabilized by the incorporation of water-soluble polymers such as polyvinyl alcohol, maltodextrin, xanthan gum, polyvinylpyrrolidone, hydroxypropyl cellulose, etc. The water-soluble polymers are preferably present in an amount of 0.5 to 20 wt %, based on the total weight of the pharmaceutical composition.

In the above-mentioned state of technology, the pharmaceutical compositions are usually prepared in such a way that candesartan cilexetil, the stabilizer and, if necessary, a binder are dispersed in water and the resulting dispersion is used as granulating liquid in the subsequent granulation stage.

Surprisingly, it has now been found that candesartan cilexetil can only be stabilized in pharmaceutical compositions by being granulated with one or more sugar alcohols, especially mannitol, in the presence of at least one binder with an alcoholic granulating liquid.

Sugar alcohols such as mannitol and sorbitol are common additives in the manufacture of solid pharmaceutical compositions. As such mannitol is often used as filler or dry binder. In addition, sugar alcohols are often used as fillers in quick-dissolving tablets because of their good water solubility.

Thus, WO 00/06126 describes a quick-dissolving pharmaceutical composition for an active ingredient such as candesartan cilexetil, which contains a sugar or sugar alcohol and low-substituted hydroxypropyl cellulose. According to WO 00/06126, the strength and dissolution rate of the pharmaceutical composition is influenced by the particle size and content of the low-substituted hydroxypropyl cellulose in the composition.

EP 1 203 580 also relates to quick-dissolving pharmaceutical compositions for candesartan cilexetil for example, containing a saccharide or a sugar alcohol with an average particle diameter of 30 um to 300 um, as well as a disintegration agent and a cellulose compound. Thus, example 6 of EP 1 203 580 describes the production of a granulate containing candesartan cilexetil, whereby the active ingredient is granulated together with mannitol, crystalline cellulose, corn starch and silica dioxide with water as granulating liquid.

It is known from U.S. Pat. No. 3,145,146 and WO 97/38960 that the compressibility of mannitol can be improved by dissolving it in water or an aqueous solvent, and followed by rapid drying, particularly by spray drying. Thus modified, it is typically used as a filler for direct tableting, in which all components of the respective tablet are dry-mixed and then compressed.

That spray-dried mannitol is also suitable for wet granulation, is described in WO 01/62230, which relates to a method for producing granulate, in which spray-dried mannitol is granulated with an aqueous solution or suspension containing the active pharmaceutical ingredient.

Given the state of technology described above, it was therefore an objective of the present invention, to provide a solid candesartan cilexetil pharmaceutical composition in the form of a tablet, whereby the active ingredient has a high degree of stability in terms of decomposition, both during storage and production of the composition.

This objective is achieved by the object specified in the claims.

It was found that storage-stable tablets containing candesartan cilexetil are obtained when they are produced by compressing granulate comprising candesartan cilexetil, a sugar alcohol and a binder, produced by granulation with an alcoholic granulating liquid.

The present invention therefore relates to granulate comprising candesartan cilexetil, a sugar alcohol and a binder, produced by granulation with an alcoholic granulating liquid.

Furthermore, the present invention relates to a method for producing a tablet containing candesartan cilexetil, which comprises the following steps:

a) Production of a granulate by granulation of a premix, comprising candesartan cilexetil, a sugar alcohol and a binder, with an alcoholic granulating liquid,
b) Drying the granulate to obtain a dry granulate, and
c) Compressing the dry granulate, if necessary with other additives, into a tablet.

The sugar alcohol contained in the granulate should preferably be less than or equal to 95 wt %, preferably about 50-95 wt %, in particular preferably 60 to 85 wt % and most preferably 65-80 wt %, based on the total weight of the granulate.

The sugar alcohols used for the manufacture of the granulate according to the present invention are in particular those which are well soluble in water, but poorly or hardly soluble in alcoholic solvents. Suitable sugar alcohols are preferably those which have four to twelve carbon atoms, such as erythritol, xylitol, sorbitol, mannitol, maltitol and lactitol as well as mixtures thereof. Particularly preferred are C6 sugar alcohols such as sorbitol and mannitol, particularly mannitol.

Binders soluble in alcoholic granulating liquid are preferably used. Preferred binders are for example polyvinylpyrrolidone, polyvinylpyrrolidone/vinyl acetate copolymer (copovidone, e.g. Plasdone S630), hydroxyethyl cellulose, hydroxypropyl cellulose, hydroxypropyl methyl cellulose, methyl cellulose or ethyl cellulose. Particularly preferred are polyvinylpyrrolidone, polyvinylpyrrolidone/vinyl acetate copolymer or a mixture of polyvinylpyrrolidone and polyvinylpyrrolidone/vinyl acetate copolymer (preferably in a mass ratio of 1:1). In the method according to the present invention, the binder can either be present in the premix exclusively or partially dissolved in the granulating liquid.

In particular, mixtures of water and an alcohol such as isopropanol or ethanol are used as an alcoholic granulating liquid, whereby the ratio of the components is chosen as to allow the sugar alcohol not to or hardly dissolve during the granulating process. On the other hand, the binder in the granulating liquid should be as readily soluble as possible. Particularly preferred are anhydrous alcoholic granulating liquids. Examples of an alcoholic granulating liquid are aqueous solutions containing as much as or more than 95 wt % alcohol, e.g. ethanol and anhydrous ethanol (equal or more than 99 wt % ethanol).

The granulate can contain other pharmaceutically acceptable additives such as fillers and disintegration agents, if necessary. As fillers may for example be used powdered cellulose, calcium diphosphate, different starches, such as corn starch, microcrystalline cellulose, silicified microcrystalline cellulose, calcium carbonate, calcium lactate, dextrose, lactose (anhydrous or as monohydrate) and the like. As disintegration agents can be used starch derivatives, cross-linked polyvinylpyrrolidone, low-substituted sodium carboxymethyl cellulose, sodium starch glycolate, microcrystalline cellulose and the like.

As a lubricant to improve the flow properties or the flowability of the tablet composition, in particular magnesium stearate, calcium stearate, sodium lauryl sulfate, Macrogol, hydrogenated castor oil, sodium stearyl fumarate, hydrogenated vegetable oil, talc and the like can be added.

The tablets produced by the granulate according to the present invention are characterized by greater stability against decomposition of the active ingredient candesartan cilexetil. Thus it was found in high-temperature studies (60° C. for ten days) that the tablet formulations described in the following examples display increased stability of the active ingredient compared to reference tablets containing candesartan cilexetil, in which the mannitol was replaced with lactose and which were granulated with water instead of alcoholic granulating liquid (ethanol).

It is believed that by using sugar alcohols, which do not or hardly dissolve in the alcoholic granulating liquid, and binders that are soluble in the granulating liquid though, a granulate is produced in which the binder envelops the sugar alcohol particles. Candesartan cilexetil is practically insoluble in water but readily soluble in alcoholic solvents. It is believed that, during the granulation process according to the present invention, candesartan cilexetil and the binder are present in the alcoholic granulating liquid in largely dissolved form, so that in the resulting granulate the active ingredient is dissolved or finely dispersed in the binder, i.e. coating the sugar alcohol in diluted form. This structure of the granulate is probably responsible for the fact that after the compression of the granulate the active ingredient is distributed homogeneously in the tablet, which means that there are no variations in the concentration of the active ingredient in different parts of the tablet. This, on the one hand, reduces the risk of separation of the tablet ingredients, on the other it minimizes the risk of a possible decomposing chain reaction of the active ingredient molecules, initiated by the decomposition of one or less candesartan cilexetil molecule(s), e.g. by heat or pressure. Decomposition of the active ingredient, if it occurs, is localized to a few molecules due to its homogeneous and fine distribution in the tablet and does not spread through the tablet in a chain reaction. Naturally, other organic solvents, which display corresponding solution properties towards sugar alcohols, the binders used and towards candesartan cilexetil, are also suitable for the granulations according to the present invention.

Moreover, the granulate according to the present invention shows good compressibility, so that relatively low pressures need to be applied during compression of the tablet mass. Thus, the mechanical stress acting on the candesartan cilexetil is reduced, minimizing the risk of decomposition of the active ingredient during tablet production.

Since water can act as a plasticizing agent in solid pharmaceutical compositions, and thus often favors the decomposition of the active ingredient, the drying of the granulate according to the present invention takes place until the moisture content in the dry granulate is equal to or less than 2 wt %, based on the total weight of the granulate.

The granulate according to the present invention is, as mentioned above already, well suited for tableting. The option exists that, apart from the granulate, other pharmaceutically acceptable additives such as lubricants, disintegration agents and fillers can be added to the tablet mass. Preferably only lubricants are added to the tablet mass, i.e. fillers and disintegration agents, if at all, are only used intragranularly. A preferred disintegration agent for the tablet according to the present invention is cross-linked polyvinylpyrrolidone (e.g. Polyplasdone XL-1 0).

If the tablet according to the present invention contains a filler in addition to the sugar alcohol, preferably starch (e.g. corn starch), then the mass ratio of the sugar alcohol to the filler should preferably be equal to or greater than 4:1.

In a particularly preferred embodiment, the tablet according to the present invention comprises candesartan cilexetil, mannitol, starch, polyvinylpyrrolidone (e.g. Plasdone K90) and polyvinylpolypyrrolidone if necessary, i.e. cross-linked polyvinylpyrrolidone or crospovidone, wherein the mass ratio of mannitol to starch is the same or greater than 4:1.

Furthermore, the granulate according to the present invention can contain one other active ingredient in addition, particularly a diuretic, e.g. hydrochlorothiazide (HCT). This other active ingredient can also be added to the tablet mass only and thus be extragranularly present in the invention-related tablet.

EXAMPLES

Example 1

1. Tablet Formulation

| Ingredients | Ex. 1a [mg] | Ex. 1b [mg] | Ex. 1c [mg] | Ex. 1d [mg] | Ex. 1e [mg] |
|---|---|---|---|---|---|
| Candesartan cilexetil | 2 | 4 | 8 | 16 | 32 |
| Mannitol | 62 | 124 | 119.94 | 110.6 | 221.2 |
| Corn starch | 10 | 20 | 20 | 20 | 40 |
| Plasdone K90 | 4 | 8 | 8 | 8 | 16 |
| Plasdone S630 | 4 | 8 | 8 | 8 | 16 |
| Magnesium stearate | 0.5 | 1 | 1 | 1 | 2 |
| Polyplasdone XL-10 | — | — | — | 1.2 | 2.4 |
| Iron oxide, red | — | — | 0.06 | 0.2 | 0.4 |
| Total weight | 82.5 | 165 | 165 | 165 | 330 |

2. Production Method

A premix of candesartan cilexetil, mannitol, corn starch, Plasdone K90, 10 Plasdone S630, if necessary Polyplasdone XL-1 0 and, if necessary, of iron oxide, red, was produced. This mixture was granulated with anhydrous ethanol. Subsequently, the granulate was dried at a temperature of about 70° C. until the moisture content in the granulate was less than 2 wt %. The granulate was ground and mixed with magnesium stearate, mixed well and compressed into tablets.

Example 2

1. Tablet Formulation

| Ingredients | Example 2a [mg] | Example 2b [mg] | Example 2c [mg] | Example 2d [mg] |
|---|---|---|---|---|
| Intragranular | | | | |
| Candesartan cilexetil | 2.00 | 2.00 | 2.00 | 2.00 |
| Mannitol | 48.88 | 51.78 | 61.26 | 55.23 |
| Corn starch | 10.00 | 10.00 | 10.00 | 10.00 |
| Xylitol | 8.25 | 4.95 | — | — |
| Sorbitol | 4.13 | 2.47 | — | — |
| Glycerin | — | 2.06 | — | 3.3 |
| Povidone (PVP K 29/32) | 4.00 | 4.00 | 4.00 | — |
| Copovidone (PVP S630) | — | — | — | 5.78 |
| Ethanol, anhydrous | q.s. | q.s. | q.s. | q.s. |
| Extragranular | | | | |
| Copovidone (PVP S630) | 4.00 | 4.00 | 4.00 | 4.95 |
| Magnesium stearate | 1.24 | 1.24 | 1.24 | 1.24 |
| Total weight | 82.50 | 82.50 | 82.50 | 82.50 |

2. Production Method

A premix was produced from the intragranular ingredients. This mixture was granulated with anhydrous ethanol or a solution of anhydrous ethanol and glycerol. Subsequently, the granulate was dried at a temperature of about 70° C. until the moisture content in the granulate was less than 2 wt %. The granulate was ground and mixed with the extragranular ingredients copovidone (PVP S630) and magnesium stearate, mixed well and compressed into tablets.

Example 3

1. Tablet Formulation

| | Quantity [%] | | | | |
|---|---|---|---|---|---|
| Ingredients | Ex. 3a 2 mg | Ex. 3b 4 mg | Ex. 3c 8 mg | Ex. 3d 16 mg | Ex. 3e 32 mg |
| Intragranular | | | | | |
| Candesartan cilexetil | | 2.43 | 4.85 | | 9.68 |
| Mannitol | | 66.95 | 67.53 | | 50.65 |
| Corn starch | | 12.12 | 12.12 | | 12.12 |
| Microcrystalline cellulose | | — | — | | 14.55 |
| Copovidone (PVP S630) | | 7.00 | 4.00 | | 7.00 |
| Glycerin | | 4.00 | 4.00 | | 5.00 |
| Ethanol, anhydrous | | q.s. | q.s. | | q.s. |
| Extragranular | | | | | |
| Copovidone (PVP S630) | | 6.00 | 6.00 | | — |
| Magnesium stearate | | 1.50 | 1.50 | | 1.00 |
| Total weight | 82.5 mg | 165 mg | 165 mg | 165 mg | 330 mg |

2. Production Method

The tablets are produced as indicated in example 2.

The invention claimed is:

1. A granulate, comprising candesartan cilexetil, a sugar alcohol and a binder, produced by granulation with an alcoholic granulating liquid.

2. The granulate according to claim 1, wherein the sugar alcohol contained in the granulate is less than or equal to 95 wt %, preferably about 50-95 wt %, based on the total weight of the granulate.

3. The granulate according to claim 1, wherein the sugar alcohol is selected from the group consisting of sorbitol, mannitol and a mixture thereof.

4. The granulate according to claim 1, wherein the alcoholic granulating liquid is anhydrous.

5. The granulate according to claim 4, wherein the alcoholic granulating liquid is anhydrous ethanol.

6. A method for producing a tablet comprising candesartan cilexetil, which comprises the following steps:
   a) Producing a granulate by granulation of a premix, comprising candesartan cilexetil, a sugar alcohol and a binder, with an alcoholic granulating liquid,
   b) Drying the granulate to obtain a dry granulate, and
   c) Compressing the dry granulate, if necessary with other additives, into a tablet.

7. The method according to claim 6, wherein the sugar alcohol comprised in the dry granulate is less than or equal to 95 wt %, preferably about 50-95 wt %, based on the total weight of the granulate.

8. The method according to claim 6, wherein the alcoholic granulating liquid is anhydrous.

9. The method according to claim 8, wherein the alcoholic granulating liquid is anhydrous ethanol.

10. The method according to claim 6, wherein the drying stage (b) lasts until the moisture content in the dry granulate is equal to or less than 2 wt %, based on the total weight of the granulate.

11. A tablet produced by compressing the granulate of claim 1.

12. The tablet according to claim 11, wherein said tablet comprises candesartan cilexetil, mannitol, starch, polyvinylpyrrolidone (povidone) and/or polyvinylpyrrolidone/vinyl acetate copolymer (copovidone) and, if necessary, polyvinylpolypyrrolidone (crospovidone), wherein the mass ratio of the mannitol to the starch is equal to or greater than 4:1.

* * * * *